United States Patent [19]
Miller

[11] Patent Number: 6,032,670
[45] Date of Patent: Mar. 7, 2000

[54] SURGICAL DRAPE FOR SHOULDER PROCEDURES

[76] Inventor: Mark T. Miller, 1132 N. County Rd. 600 E., Danville, Ind. 46122

[21] Appl. No.: 09/082,259

[22] Filed: May 20, 1998

Related U.S. Application Data

[60] Provisional application No. 60/047,241, May 21, 1997.

[51] Int. Cl.⁷ .................................................. A61B 19/00
[52] U.S. Cl. .......................................... 128/849; 128/853
[58] Field of Search ..................... 128/849–856

[56] References Cited

U.S. PATENT DOCUMENTS

| | | | |
|---|---|---|---|
| 4,119,093 | 10/1978 | Goodman | 128/856 |
| 4,890,628 | 1/1990 | Jackson | 128/849 |
| 4,905,710 | 3/1990 | Jones | 128/849 |
| 4,957,120 | 9/1990 | Grier-Idris | 128/849 |
| 5,002,069 | 3/1991 | Thompson et al. | 128/849 |
| 5,109,873 | 5/1992 | Marshall | 128/849 |
| 5,143,091 | 9/1992 | Patnode et al. | 128/853 |
| 5,161,544 | 11/1992 | Morris | 128/849 |
| 5,322,071 | 6/1994 | Ambrose | 128/849 |
| 5,345,946 | 9/1994 | Butterworth et al. | 128/853 |
| 5,419,343 | 5/1995 | Taylor | 128/849 |
| 5,494,050 | 2/1996 | Reyes | 128/849 |
| 5,513,655 | 5/1996 | Peimer et al. | 128/849 |
| 5,871,014 | 2/1999 | Clay | 128/853 |

OTHER PUBLICATIONS

Product brochure entitled Convertors/Custom Sterile Product Guide, Baxter Healthcare Corporation, McGaw Park, IL, 1992.
Product catalog entitled Advanced Protection Through Innovation, Kimberly–Clark, Roswell, GA, 1995.
Product brochure entitled Orthoarts Shoulder Arthroscopy Fluid Control Pack, Kimberly–Clark, Roswell, GA, 1994.

*Primary Examiner*—Michael A. Brown
*Attorney, Agent, or Firm*—Baker & Daniels

[57] ABSTRACT

A drape for surgical procedures on a shoulder. The drape includes a flexible sheet of fluid impervious material intended to overlay a patient arranged in either a lateral position or a beach chair position. The sheet includes a shoulder accommodating fenestration, and the resilient construction of the sheet around the fenestration causes the sheet to generally conform to a patient's shoulder area after the patient's arm is inserted through the fenestration. A pair of fluid collection pouches are connected to the sheet in a fluid tight fashion on opposite sides of the fenestration, and are arranged such that fluids present at the shoulder during the surgical procedure flow by gravity into one or both of the fluid collection pouches. A method of draping a patient for shoulder surgery is also disclosed.

19 Claims, 7 Drawing Sheets

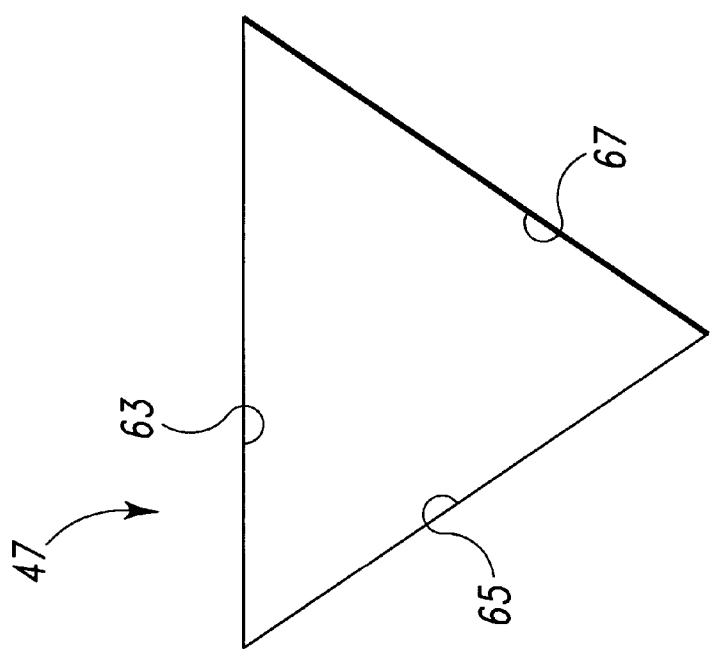
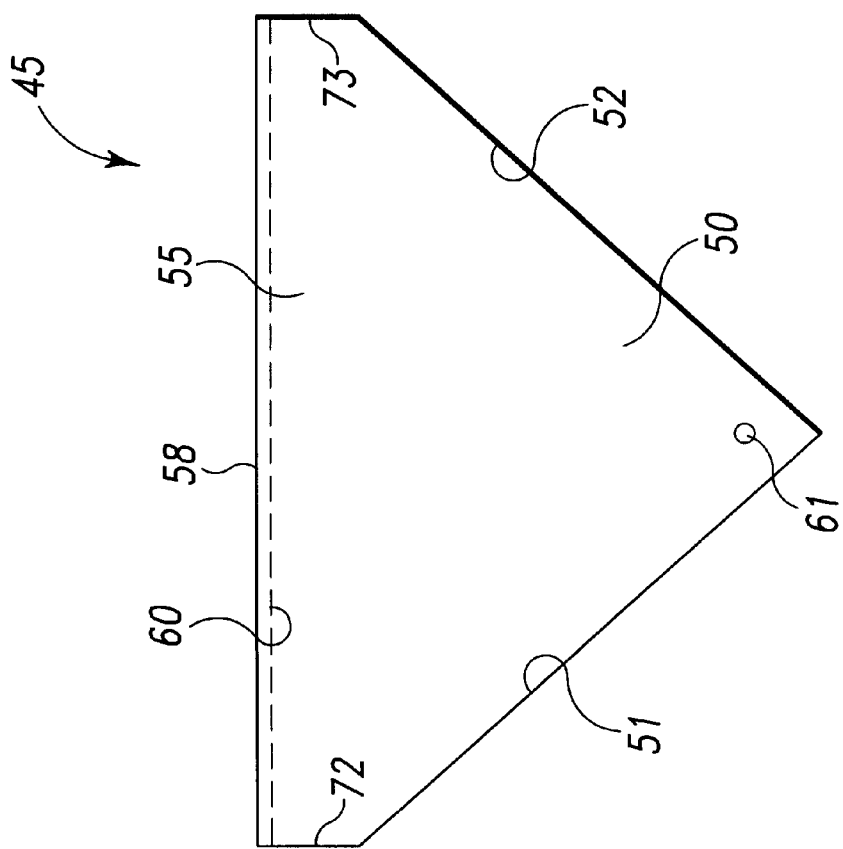
Fig. 4B
Fig. 4A

SURGICAL DRAPE FOR SHOULDER PROCEDURES

CROSS-REFERENCE TO RELATED APPLICATION

This application claims the benefit under 35 U.S.C. § 119(e) of U.S. Provisional Application No. 60/047,241, filed May 21, 1997.

BACKGROUND OF THE INVENTION

The present invention pertains to surgical drapes, and, in particular, to a surgical drape adapted for use during the performance of surgery on a shoulder.

An assortment of differently configured surgical drapes are known in the art. Many drapes have been specifically developed or customized for use in particular surgical procedures, such as for knee surgery or for operative procedures on body extremities. These drapes are configured to isolate the surgical field or site while simultaneously providing ready access to the patient's body part requiring medical attention. And, surgical drapes frequently include a fluid collection pouch intended to contain and control fluids introduced to or emanating from the surgical field.

One problem with many currently available surgical drapes for shoulder procedures is their failure to provide adequate coverage of some patients. Moreover, the available shoulder surgery drapes typically do not provide fluid collection systems capable of fully removing fluid run-off from the surgical site. Consequently, due to this insufficient fluid management, operating room personnel are constantly getting their legs and feet wetted by the surgical fluids. Not only may it reach the physician and his or her assistants, but the fluid also may drain onto the patient, thereby compromising the sterile technique and validity of the sterile field. In today's society where contamination by bloodborne pathogens is of increasing concern, properly containing the surgical fluids is highly desirable.

Thus, it would be desirable to provide a surgical drape which overcomes these and other shortcomings of the prior art.

SUMMARY OF THE INVENTION

The present invention provides a suitably sized surgical drape with sufficiently large and properly positioned fluid collecting bags or pouches adapted for use with a patient undergoing shoulder surgery. By employing fluid collection pouches on both sides of a fenestration through which the shoulder of a patient is accessed, the surgical drape is readily adapted for use with patients positioned in either a conventional beachchair position or a lateral position.

In one form thereof, the present invention provides a shoulder surgery drape including a flexible sheet adapted for placement over a patient and which includes a fenestration for receiving therethrough an arm of a patient inserted a sufficient distance to expose a shoulder area of the patient, a first fluid collection pouch attached to the sheet and positioned proximate the fenestration for collecting fluid associated with surgery, and a second fluid collection pouch attached to the sheet and positioned proximate the fenestration for collecting fluid associated with surgery, wherein the first and second pouches are disposed on opposite portions of the fenestration.

In another form thereof, the present invention provides a surgical drape for shoulder procedures including a flexible sheet sized and configured to overlay at least a substantial portion of a patient arranged in either a lateral position or a beach chair position, wherein the flexible sheet includes a shoulder accommodating fenestration and a resilient construction around the fenestration such that the sheet generally conforms to a shoulder of the patient after an arm of the patient is inserted through the fenestration, a first pouch connected to the sheet in a fluid tight fashion on a first side of the fenestration for collecting fluid present on the sheet proximate the fenestration during use, and a second pouch connected to the sheet in a fluid tight fashion on a second side of the fenestration for collecting fluid present on the sheet proximate the fenestration during use.

In still another form thereof, the present invention provides a method of draping a patient for shoulder surgery including the steps of arranging the patient in either a lateral position or a beach chair position, and providing a drape comprising a flexible sheet including a fenestration, and a pair of fluid collection pouches sealingly attached to the sheet on opposite sides of the fenestration. The method further includes the steps of placing the drape over the patient such that an arm of the patient inserts through the fenestration a sufficient distance to expose a shoulder area of the patient, and such that the patient is generally covered by the flexible sheet, and arranging the drape previously placed over the patient such that fluids present at the shoulder area of the patient during surgery flow by gravity into one or both of the fluid collection pouches.

One advantage of the present invention is that a surgical drape for a shoulder procedure is provided which has a fluid collection system of adequate size and shape to control fluid run-off so as to limit potential exposure of operating room personnel to the fluid associated with the surgical procedure.

Another advantage of the present invention is that the surgical drape is suited for surgical procedures on either the left or right shoulder of a patient.

Still another advantage of the present invention is that a single surgical drape can be utilized with differently positioned patients.

Yet another advantage of the present invention is that a shoulder surgery drape is provided that is strong and durable so as to not break down or rip during normal use.

BRIEF DESCRIPTION OF THE DRAWINGS

The above mentioned and other advantages and objects of this invention, and the manner of attaining them, will become more apparent and the invention itself will be better understood by reference to the following description of embodiments of the invention taken in conjunction with the accompanying drawings, wherein:

FIGS. 4A and 4B are top views of first and second component pieces that when assembled together form a fluid collection pouch;

Figure 1:
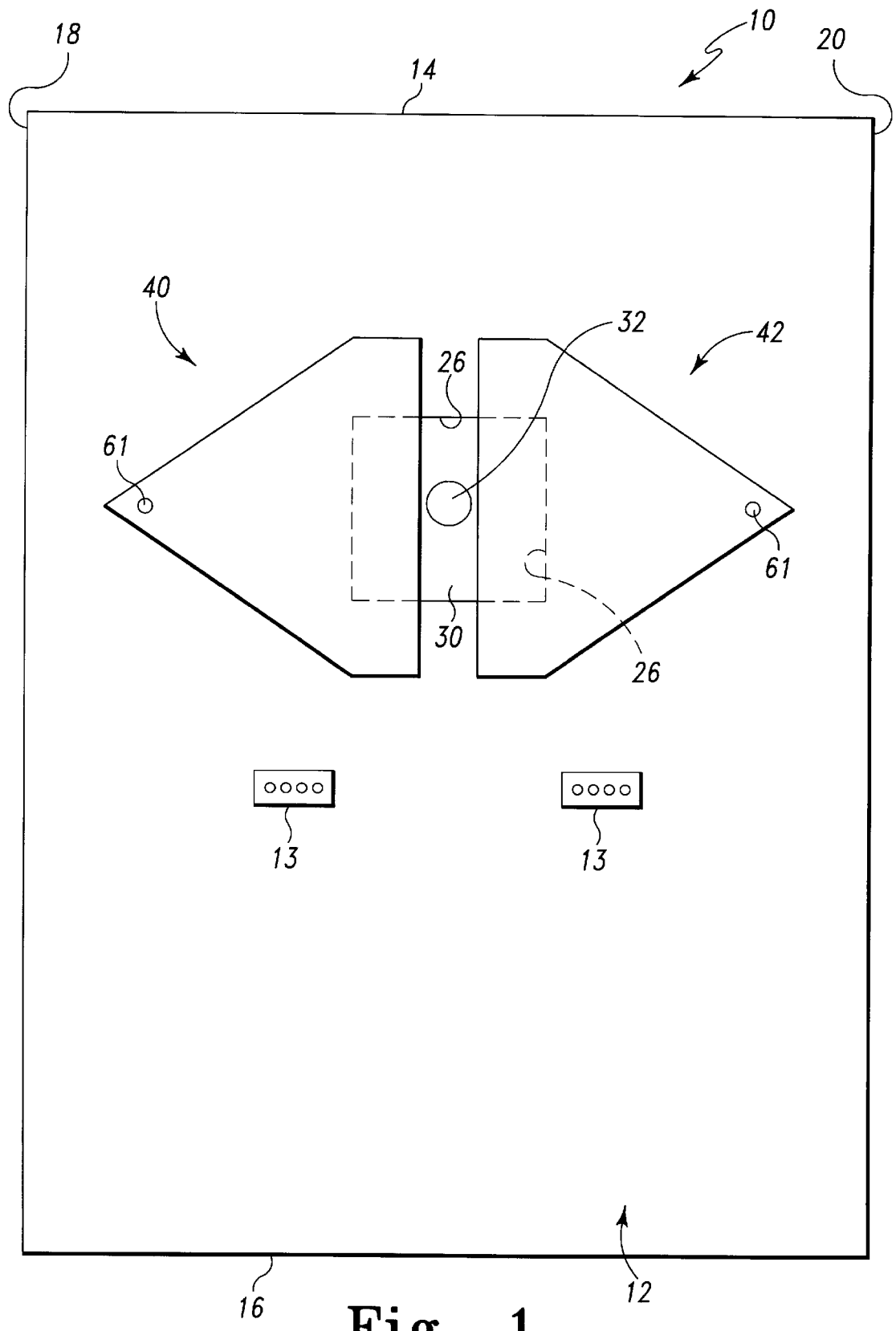
FIG. 1 is a top view showing the surgical drape according to a first embodiment of the present invention arranged in a planar, or fully unfolded, position prior to its placement over a patient.

Corresponding reference characters indicate corresponding parts throughout the several views. Although the drawings represent embodiments of the invention, the drawings are not necessarily to scale and certain features may be exaggerated or omitted in order to better illustrate and explain the present invention.

DESCRIPTION OF THE PREFERRED EMBODIMENTS

Referring now to FIG. 1, there is shown a top view of a one-use or disposable surgical drape, generally designated 10, configured according to a first embodiment of the present invention. Surgical drape 10 comprises a base or main sheet 12 sized and shaped to fully cover, from head to toe, a patient when drape 10 is placed over that patient to isolate the patient's shoulder for surgery. In the shown embodiment, sheet 12 is rectangularly shaped and has a length measuring approximately one hundred eight inches from top edge 14 to bottom edge 16, and a width measuring about eighty-four inches from side edge 18 to side edge 20. This shaped and sized sheet is believed sufficiently large to adequately cover in a non-cumbersome fashion most patients who are candidates for its use.

Sheet 12 is made of a flexible material that is fluid impervious so as to not absorb fluids which land thereon during use. Sheet 12 serves as a protective barrier that has low lint generation characteristics, is flame retardant, is impervious to strikethrough, and is preferably latex free. Any one or more of a variety of materials, including disposable surgical papers, non-woven materials or fabrics, polypropylene, and others that are known to be used for the bases of other surgical drapes, may be employed as sheet 12. Cord stays 13, which are formed as apertured flaps extending from sheet 12, are positioned to aid in holding instruments that may be employed in the surgical procedure.

Figure 3:
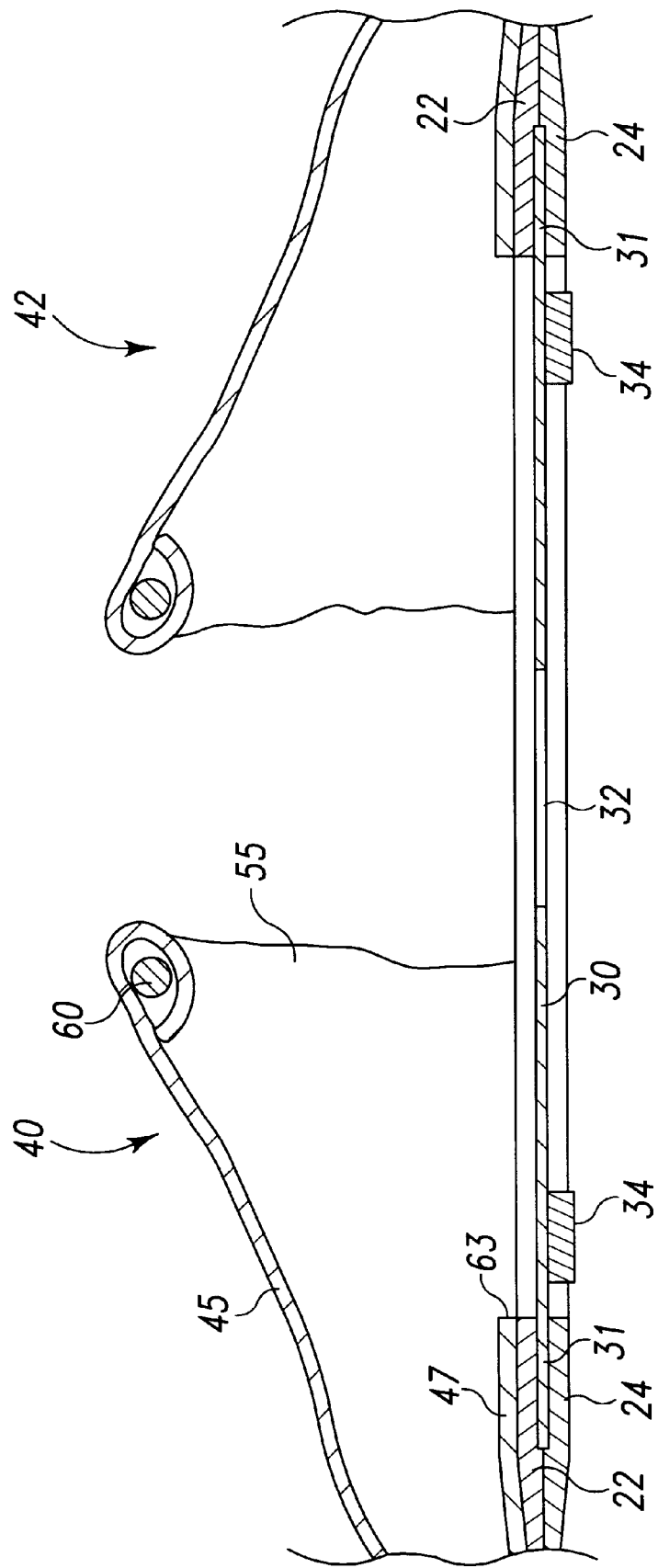
FIG. 3 is a cross-sectional side view taken along line 3—3 of FIG. 2 diagrammatically showing a preferred drape construction.

As shown in the cross-sectional view of FIG. 3, sheet 12 is formed of a top layer 22 and a bottom layer 24 which are identically shaped, sized and constructed. Top layer 22 and bottom layer 24 are glued together along the lengths of top edge 14, bottom edge 16, and side edges 18 and 20 to prevent separation of the layers. At a location spaced about thirty inches from top edge 14 and centered between side edges 18 and 20, sheet top layer 22 and bottom layer 24 each include a square opening 26 therethrough that is shown in dashed and solid lines in FIG. 1. One suitable opening measures eighteen inches by eighteen inches, but larger or smaller dimensioned openings may be employed within the scope of the invention.

Spanning opening 26 is a sheet 30 of a flexible, resilient and elastomeric or rubber-like material that is fluid impervious. Sheet 30, which is preferably latex free, includes a centrally located, small fenestration 32 adapted to allow passage therethrough of the arm of the person whose shoulder is to be worked on with drape 10. In the shown embodiment, fenestration 32 is a four inch diameter, circular hole, but differently sized or shaped holes may be provided. The elastomeric construction of sheet 30 allows it to conform to the shape of the shoulder area disposed within fenestration 32 to better ensure a relatively fluid tight seal against the patient's skin.

Figure 2:
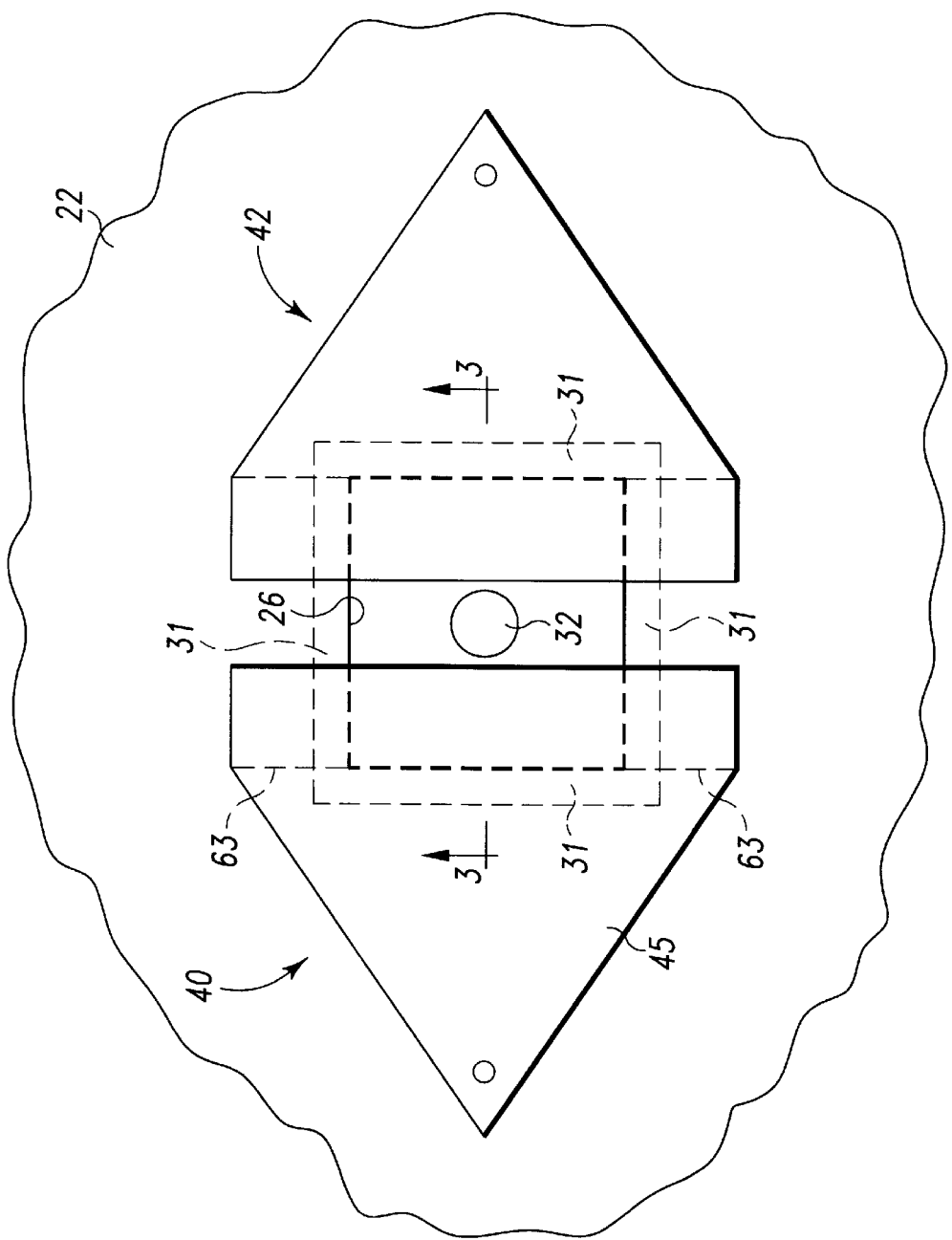
FIG. 2 is an enlarged view of a portion of the drape of FIG. 1.

Sheet 30 comprises a twenty-four inch square flat piece of material that is centered within main sheet opening 26. As shown in FIGS. 2 and 3, along each of its four sides, a three inch wide portion 31 of sheet 30 is sandwiched between main sheet top layer 22 and bottom layer 24. Sheet portions 31 are secured to base sheet layers 22 and 24 in a manner to prevent fluid penetration therebetween. A preferred form of securement is via gluing, but other securement techniques, such as stitching, may be employed within the scope of the invention.

Mounted on the underside surface of sheet 30 are adhesive strips 34 (See FIG. 3). Adhesive strips 34 are latex free and completely ring fenestration 32. Adhesive strips 34 are covered by a release paper (not shown) when drape 10 is not being used, and the release paper may be peeled off to expose adhesive strips 34 to allow drape 10 to be attached to the skin of the patient to prevent drape 10 from moving or shifting on the patient during use.

Flanking the fenestration on either side are two separate fluid collection pouches generally designated 40 and 42. Pouches are placed between the side edges of drape 10 and the fenestration to collect fluids that run off from the surgical site as described further below.

With additional reference to FIGS. 4A and 4B, one suitable construction of pouch 40 will be further described. It will be appreciated that as pouch 42 is a mirror-image of pouch 40, the following further explanation of pouch 40 has equal application to pouch 42. Pouch 40 includes a top layer 45 shown in FIG. 4A and a bottom layer 47 shown in FIG. 4B. Top and bottom layers 45 and 47 are formed of a flexible, fluid impervious material such as plastic. Top layer 45 includes a triangular-shaped bottom region 50, defined by edges 51 and 52, and a rectangular-shaped upper region 55 at the top of bottom region 50. At its top edge 58, upper region 55 has attached thereto, such as by being sealed within an turned under lip of top layer 45 as shown in FIG. 3, a coated wire 60. Wire 60 runs the entire length of upper region 55 and is moldable to allow the upper lip of pouch layer 45 to be maintained in a bowed outward shape in spaced apart relationship from sheet 12 during use as shown in FIG. 3 to allow fluids to flow into pouch 40. In the embodiment shown in FIG. 1, the triangular-shaped bottom region 50 is an isosceles triangle in shape having dimensions of fifty-seven inches along its base, and twenty-nine inches along its two other sides, and upper region 55 measures approximately six inches by fifty-seven inches.

Formed at the base of bottom region 50 is a suction connector diagrammatically represented at 61. Any of a variety of known types of connectors which allow for a fluid connection to a tubing for drainage of the fluids collected in pouch 40 may be employed within the scope of the invention. For example, one known type of connector is a plastic, hollow cone formed with external hose barbs. Prior to surgery, the end of the cone is clipped off such that the cone hollow is exposed, and tubing is attached onto the connector via the hose barbs to allow fluid to drain from the pouch 40 through the connector 61 and through the attached drainage tubing.

Bottom layer 47 is an isosceles triangle in shape and includes a top edge 63 and side edges 65 and 67. In the embodiment shown in FIG. 1, top edge 63 measures approximately thirty-two inches, and each of side edges 65 and 67 measures approximately twenty-nine inches. During construction of pouch 40, along their entire lengths, side edge 65 and side edge 67 are connected in a fluid tight manner to top layer edges 51 and 52, respectively. This fluid tight seal may be effected via glue or a heat seal or other manners known in the art. As a result of this sealing connection, fluids may be collected in this pouch formed between layers 45 and 47. And, because upper region 55 is longer than top edge 63, even when bottom layer 47 lies flat against sheet 12, top layer 45 may bow out to form an adequately sized mouth into which fluids may flow. Alternative pouch constructions, such as a one-piece construction, may be employed within the scope of the present invention. In addition, a still further alternative pouch construction utilizes the upper surface of sheet 12 as the back of the pouch, and would be achieved by sealingly attaching top layer 45 directly to the fluid impervious sheet 12.

To assemble pouch 40 to sheet 12, along its entire length, top edge 63 is glued to main sheet top layer 22 as shown in FIG. 3. As shown in dashed lines in FIG. 2, top edge 63 is positioned along the edge of sheet opening 26 so as to be at the exposed edge of elastomeric sheet 30. The lateral portions of pouch top layer 45 that are at and immediately adjacent to upper region edges 72, 73, and which also directly abut top edge 63, are also glued in a fluid-tight fashion to sheet top layer 22 along their entire heights. Upper region edges 72 and 73 are configured such that when pouch 40 is used to collect fluids, these edges are positioned at a height above the lower edge of sheet 30 at which the bottom layer 47 of pouch 40 is disposed. In other words, if the edge of sheet 30 along which the pouch bottom layer is disposed is considered the bottom edge, pouch edges 72 and 73 flank the side edges of sheet 30. This gluing provides a fluid tight seal to prevent fluid from leaking between pouch top edge 63 and sheet layer 22, and the edges 72, 73 and sheet layer 22.

Figure 5:
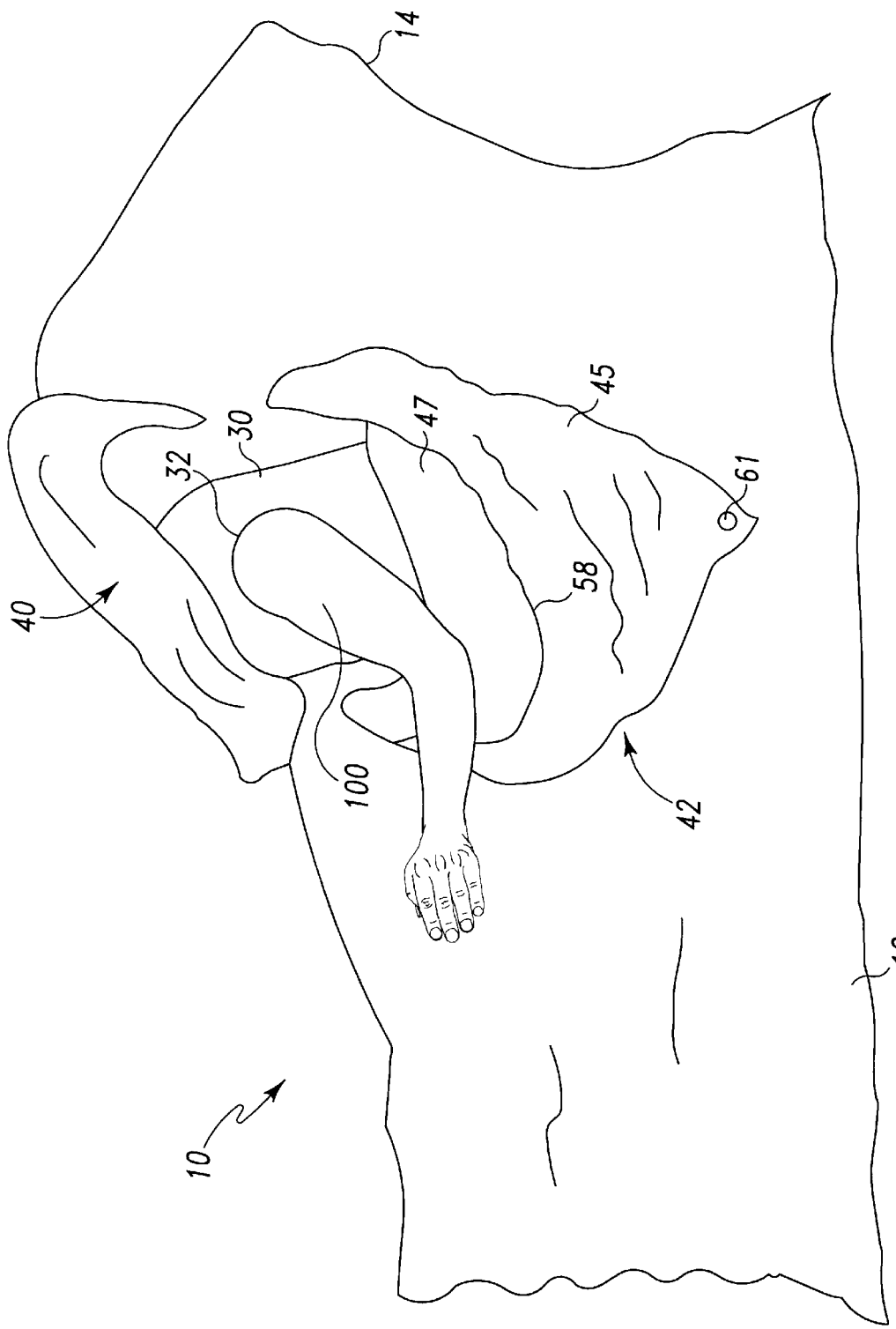
FIG. 5 is a side view of the surgical drape of FIG. 1 operationally positioned over a patient arranged in a beachchair or reclining position for surgery.

The structure of the present invention will be further understood in view of the following explanation of its operation. In FIG. 5, there is shown surgical drape 10 overlaying a patient seated in the beachchair position. The patient's left arm 100 has been inserted through fenestration 32 in the elastomeric sheet 30 to such an extent that the patient's shoulder is exposed through fenestration 32. The sheet 30 has stretched to allow fenestration 32 to accommodate the larger diameter human limb. When drape 10 is so arranged, fluid either introduced to (such as irrigating saline solution) or emanating from (such as blood) the surgical site, drains by gravity from the surgical site along sheet 30 and over the upper lip of the pouch bottom layer 47 and into pouch 42. Top layer edge 58 is spaced from layer 47 due to the contained wire 60 to keep pouch 42 open. The fluid may be drained through tubing (not shown) attached to connector 61. In this configuration, the opposite pouch 40 is not required due to the positioning of the patient, and is simply laid over the portion of the drape overlaying the patient's head so as to be out of the way of the surgical personnel. It will be appreciated that if a patient's right shoulder were to require surgical attention, the patient's right arm would be inserted into the fenestration 32, and pouch 40, rather than pouch 42, would be employed to contain and collect fluid from the surgical site in a manner similar to that shown in FIG. 5.

Figure 6:
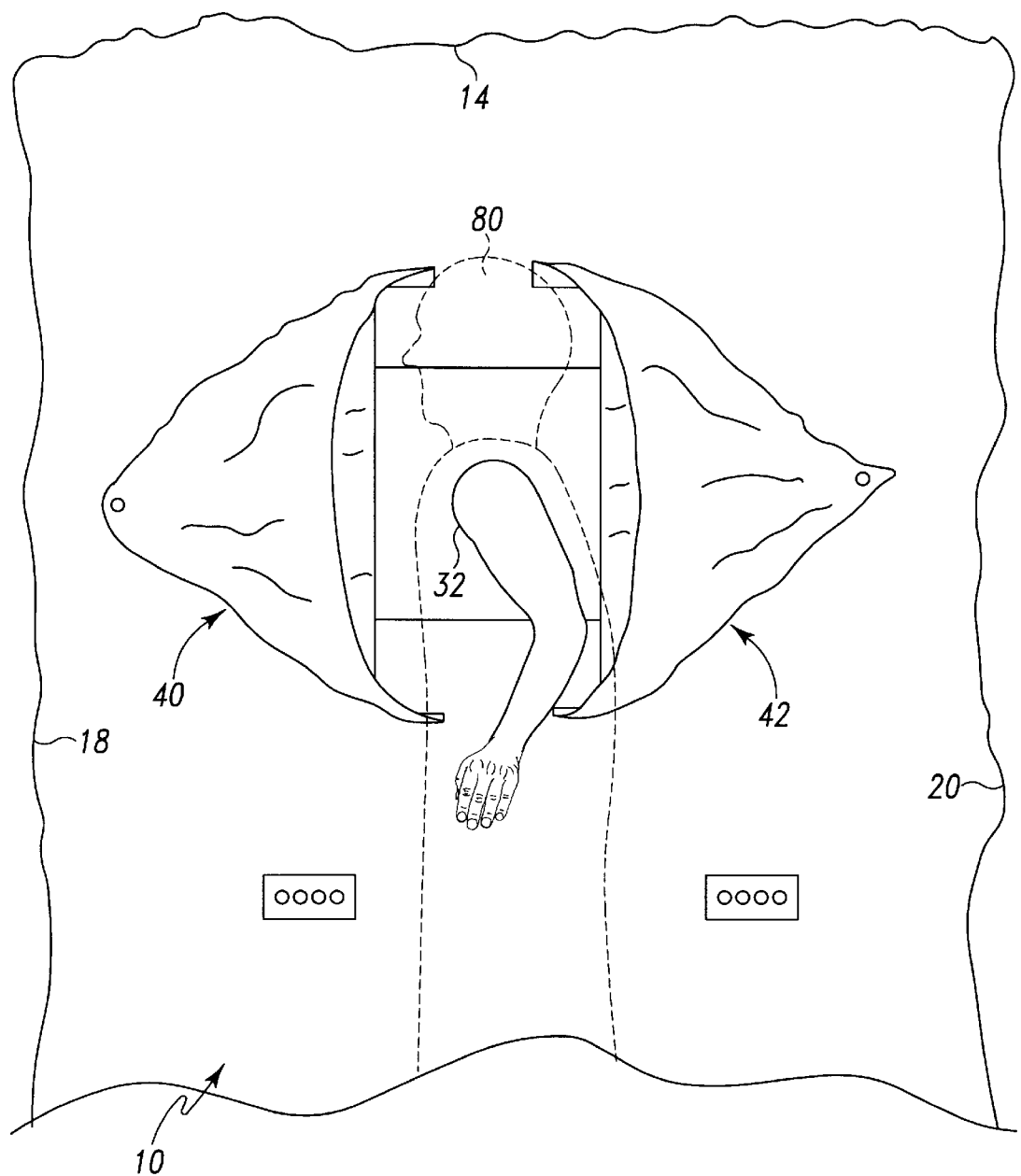
FIG. 6 is a top view of the surgical drape of FIG. 1 operationally positioned over a patient arranged in a lateral position.

Referring now to FIG. 6, there is shown a top view of another operational configuration of surgical drape 10. In this embodiment, the patient 80 is shown in dashed lines arranged on an operating table on his/her side or in a lateral position. The upwardly facing arm and shoulder has been passed through fenestration 32 in a manner similar to the manner described with respect to FIG. 5 so as to be accessible. In this embodiment, both pouches 40 and 42 are utilized to collect fluid, thereby preventing fluid from draining off either side of the patient. This two pouch configuration allows a single drape to be used even when the shoulder is positioned at the highest point of the patient's body.

Figure 7:
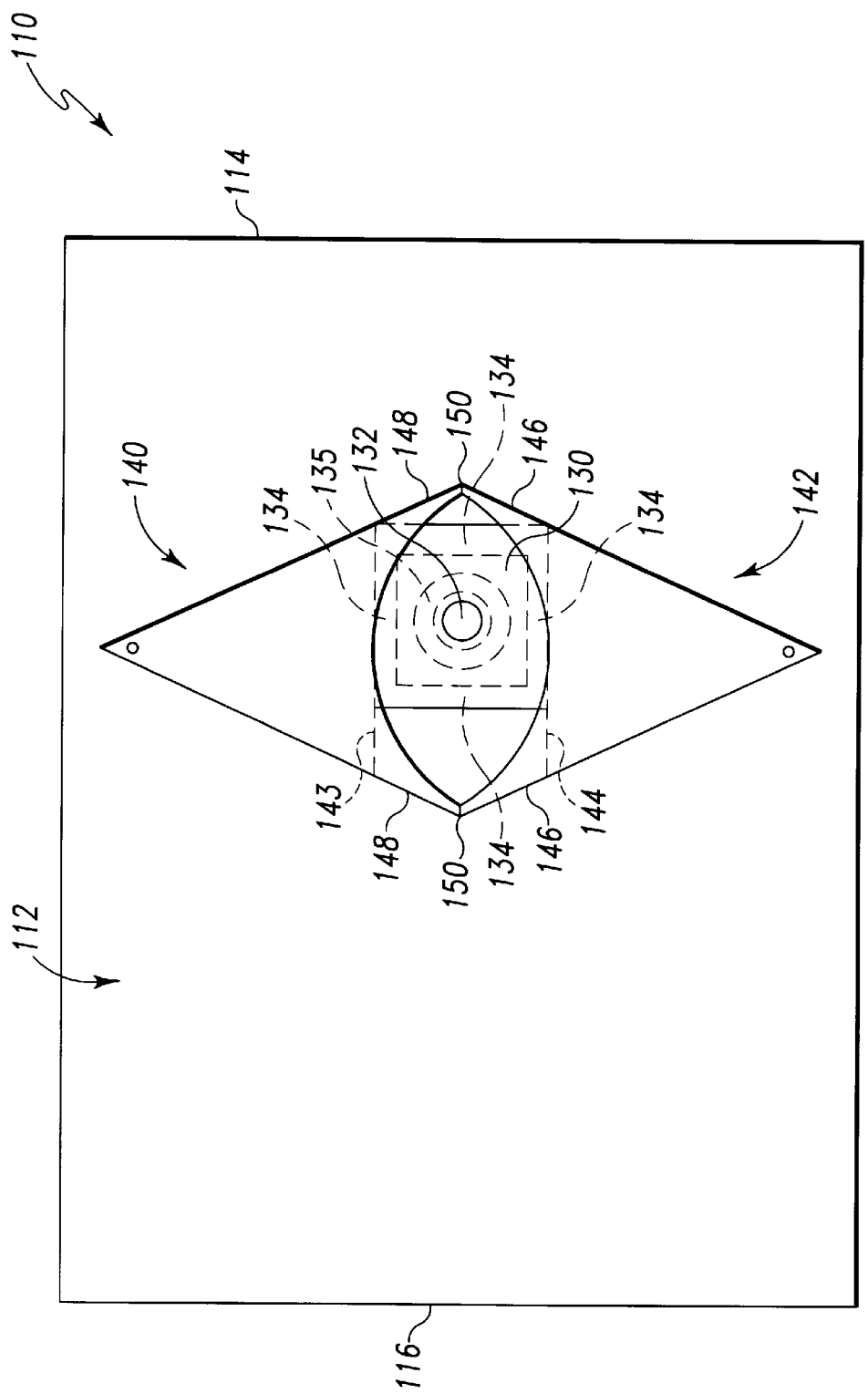
FIG. 7 is a top view showing a surgical drape according to a second embodiment of the present invention arranged in an unfolded position prior to its placement over a patient for surgery.

Referring now to FIG. 7, there is shown a top view of a second embodiment of the present invention, generally designated 110, which is configured and constructed in many respects similar to drape 10 but which, in part due to its manner of manufacture, slightly differs from the design of drape 10 as further described below. Drape 110 comprises a patient-covering sheet 112 having a patient head-to-toe covering length measuring approximately one hundred nine inches, and a width measuring approximately seventy-nine inches. Sheet 112, which includes the same properties as sheet 12 such as a fluid impervious construction, may be made from any of a variety of materials known in the drape art, and one such material is a non-woven fabric commercially available from Dexter Nonwovens of Windsor Locks, Conn. Sheet 112 may be provided as a single sheet of material or fabric, or alternatively as multiple sheets of material in a layered arrangement. A thirteen and one-half inch square fenestration or opening through sheet 112 is provided at a location that begins approximately thirty-two and one-fourth inches from the edge 114 of sheet 112 proximate the patient's head, and which is centered along the width of sheet 112.

Secured over the opening in sheet 112 is an eighteen inch square sheet 130 of an elastomeric, fluid impervious and latex-free material. One suitable material is a 5.0 mil film composed of an anti-static, thermoplastic rubber compound commercially available as Elastoflex® K from Clopay Plastics Co. of Cincinnati, Ohio. Sheet 130 is secured in a fluid-tight fashion to the top surface of sheet 112 by adhesive strips, abstractly shown in dash lines at 134, positioned on the underside of sheet 130. Adhesives 134 completely ring the perimeter of sheet 130. A circular, shoulder accommodating fenestration 132, having a diameter of approximately four inches, is provided through sheet 130. A two-inch wide adhesive ring, abstractly shown in dashed lines at 135, is sealingly attached to the underside of sheet 130 and is covered by a release paper (not shown) on its downward facing surface. The release paper may be peeled off to allow a fluid-tight attachment of adhesive 135 to the skin of the patient, thereby preventing leakage from the surgical site onto the patient outside the surgical field and underneath drape 110.

Laterally disposed of fenestration 132 are a pair of fluid collection pouches, generally designated 140 and 142, that serve to collect fluids impinging on drape 110 during surgical procedures. Each of pouches 140 and 142 is formed by sealingly connecting together top and bottom layers of fluid impervious plastic in a manner similar to the manufacture of pouches for the embodiment of FIGS. 1 through 6. In the embodiment of FIG. 7, the top layer of each pouch is formed with a rectangular top or fenestration proximate region having a width measuring approximately fifty-one inches and a height measuring approximately four inches, and the distance from the fifty-one inch top edge to the apex of the triangular bottom region of the top layer is approximately thirty-four inches. The back layer of each pouch is provided by a piece of material in the shape of an equilateral triangle having sides measuring approximately twenty-six inches. It will be recognized that in this second embodiment, when the pouch layers are sealingly connected during manufacture, the portion of the bottom region of the top layer that is proximate the top layer top region projects beyond the bottom layer. A quarter-inch wire is sealed into a one-inch flap of the top layer and allows each pouch top layer to be maintained in a bowed condition in order to keep the pouches open during use.

The top or mouth opening edge portions 143 and 144 of the bottom layers of pouches 140 and 142, respectively, are each sealingly attached to sheet 112 at the edge of sheet 130 via two-inch wide strips of double-sided tape or adhesive that run along the entire pouch top edges. The side edge portions indicated at 146 and 148, respectively, of the pouch top layers which extend toward the centerline of drape 110 beyond the pouch bottom layers are each secured to sheet 112 via a one-inch strip of adhesive that ends at the adhesives used to connect the pouch bottom layers to sheet 112. The top three inches of each side edge portion 146 is also sealingly attached at 150 to the top three inches of the side edge portion 148 which it faces. The one-inch adhesive strips attaching pouch side edge portions 146 and 148 to sheet 112 abut each other. This sealing abutment results in a fluid tight seal between sheet 112 and the pouches 140 and 142 that completely rings fenestration 132 in spaced relationship therewith, and prevents fluids draining along sheet 130 and sheet 112 from reaching the operating room floor. Pouches 140 and 142 are secured to sheet 112 at a location such that fenestration 132 is offset relative thereto, such as about two and one-half inches, toward the patient's head covering portion of sheet 112. This offsetting allows for more suitable accommodation of fluid when a patient is disposed in a beach chair position.

As with the pouches of the embodiments of FIGS. 1 through 6, suction connectors are provided in pouches 140 and 142 for drainage purposes. Although not shown, a single cord stay centrally positioned along the width of sheet 112 at a lengthwise position between fenestration 132 and sheet edge 116 may be provided to hold instruments employed in the surgical procedure.

While this invention has been shown and described as having multiple designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A shoulder surgery drape comprising:
   a flexible sheet adapted for placement over a patient, said sheet comprising a fenestration for receiving therethrough an arm of a patient inserted a sufficient distance to expose a shoulder area of the patient;
   a first fluid collection pouch attached to said sheet and positioned proximate said fenestration for collecting fluid associated with surgery; and
   a second fluid collection pouch attached to said sheet and positioned proximate said fenestration for collecting fluid associated with surgery, wherein said first and second pouches are disposed on opposite portions of said fenestration.

2. The shoulder surgery drape of claim 1 wherein said sheet comprises a length and a width, said length extending between a first end edge and a second end edge, said first end edge adjacent a sheet portion overlayable a head of the patient, said second end portion adjacent a sheet portion overlayable a torso and lower extremities of the patient, said width extending between a first side edge and a second side edge, wherein said first fluid collection pouch is disposed between said fenestration and said first side edge, and wherein said second fluid collection pouch is disposed between said second side edge and said fenestration.

3. The shoulder surgery drape of claim 2 wherein said first and second fluid collection pouches are constructed and sealingly attached to said sheet so as to provide a fluid-tight barrier on a top surface of said sheet completely ringing said fenestration.

4. The shoulder surgery drape of claim 1 wherein said sheet comprises a first sheet portion and a second sheet portion substantially covering an opening provided through said first sheet portion, wherein said fenestration extends through said second sheet portion, and wherein said second sheet portion comprises a resilient construction to conform to a shape of the shoulder area of the patient.

5. The shoulder surgery drape of claim 4 further comprising an adhesive ring sealingly attached to an underside of said second sheet portion and extending circumferentially around said fenestration, said adhesive ring attachable to the patient in a fluid tight relationship.

6. A shoulder surgery drape comprising:
   a flexible sheet sized and configured to overlay at least a substantial portion of a patient arranged in either a lateral position or a beach chair position;
   wherein said flexible sheet comprises a shoulder accommodating fenestration, said flexible sheet comprising an elastic construction completely ringing said fenestration such that said sheet generally elastically conforms to a shoulder of the patient after an arm of the patient is inserted through said fenestration to provide a substantially fluid tight seal against the patient;
   a first pouch for collecting fluid present on said sheet proximate the fenestration during use, said first pouch connected to said sheet in a fluid tight fashion on a first side of said fenestration; and
   a second pouch for collecting fluid present on said sheet proximate the fenestration during use, said second pouch connected to said sheet in a fluid tight fashion on a second side of said fenestration.

7. The shoulder surgery drape of claim 6 wherein said first side of said fenestration is opposite said second side of said fenestration.

8. The shoulder surgery drape of claim 7 wherein said sheet comprises a length and a width, wherein said length is operationally arrangeable to extend along a head-to-toe height of the patient, said width extending between a first side edge and a second side edge, wherein said first pouch is disposed between said first side edge and said fenestration, and wherein said second pouch is disposed between said second side edge and said fenestration.

9. The shoulder surgery drape of claim 8 wherein each of said first pouch and said second pouch comprises a means for maintaining said pouch open during use such that fluid draining along said sheet flows into said pouch for collection.

10. The shoulder surgery drape of claim 8 wherein said first and second pouches are connected to said sheet in a fluid tight fashion around the entire circumference of said fenestration.

11. The shoulder surgery drape of claim 8 wherein said first and second fluid collection pouches are each formed with an upper layer portion and a lower layer portion that define therebetween a pouch volume, said lower layer portion being generally between said upper layer portion and said sheet, wherein a first edge of said lower layer portion proximate said fenestration is sealingly connected to said sheet, and wherein a region of said upper layer portion projecting toward said fenestration beyond said first edge of said lower layer portion comprises first and second lateral portions sealingly connected to said sheet.

12. The shoulder surgery drape of claim 11 wherein said first and second lateral portions of said upper layer portion of said first pouch are respectively sealingly attached to said first and second lateral portions of said upper layer portion of said second pouch.

13. The shoulder surgery drape of claim 8 wherein along the length of said sheet and relative to said first and second pouches, said fenestration is offset toward a patient head-covering region of said sheet.

14. The shoulder surgery drape of claim 8 wherein said flexible sheet comprises a first sheet portion made of a fluid impervious material and including an opening, and a second sheet portion attached to said first sheet portion over said opening, wherein said second sheet portion is a fluid impervious, latex-free, resilient material and comprises said fenestration.

15. The shoulder surgery drape of claim 14 wherein said second sheet portion is adhesively attached to said first sheet portion in a fluid tight fashion.

16. The shoulder surgery drape of claim 8 further comprising an adhesive ring for providing a fluid tight seal between said sheet and the patient, said adhesive ring mounted to an underside surface of said sheet around said fenestration.

17. A method of draping a patient for shoulder surgery, comprising the steps of:

arranging the patient in either a lateral position or a beach chair position;

providing a single drape comprising a flexible sheet including a fenestration, and a pair of fluid collection pouches sealingly attached to the sheet on opposite sides of the fenestration, wherein said pair of fluid collection pouches are constructed and sealingly attached to said sheet so as to provide a fluid-tight barrier on a top surface of said sheet completely ringing said fenestration;

placing the single drape over the patient such that an arm of the patient inserts through the fenestration a sufficient distance to expose a shoulder area of the patient, and such that the patient is generally covered by the flexible sheet; and arranging the drape previously placed over the patient such that fluids present at the shoulder area of the patient during surgery flow by gravity into one or both of the fluid collection pouches.

18. The method of claim 17 wherein the patient arranging step comprises arranging the patient in a beach chair position, and wherein the drape arranging step comprises layering one of the fluid collection pouches over the sheet covered head of the patient in a manner which precludes collection of fluid within such layered pouch.

19. The method of claim 17 wherein the drape providing step comprises providing a drape suitable for use in both a surgical procedure on a right shoulder and a surgical procedure on a left shoulder.

* * * * *

UNITED STATES PATENT AND TRADEMARK OFFICE
CERTIFICATE OF CORRECTION

PATENT NO. : 6,032,670
DATED : March 7, 2000
INVENTOR(S) : Mark T. Miller

It is certified that error appears in the above-identified patent and that said Letters Patent is hereby corrected as shown below:

In column 7, line 52, after ";", delete "and".

In column 7, line 57, after "fenestration", insert --; and wherein said first and second fluid collection pouches are constructed and sealingly attached to said sheet so as to provide a fluid-tight barrier on a top surface of said sheet completely ringing said fenestration--.

In column 8, line 3, delete "3. The shoulder surgery drape of claim 2 wherein said first and second fluid collection pouches are constructed and sealingly attached to said sheet so as to provide a fluid-tight barrier on a top surface of said sheet completely ringing said fenestration."

Signed and Sealed this

Thirteenth Day of February, 2001

*Attest:*

NICHOLAS P. GODICI

*Attesting Officer*     Acting Director of the United States Patent and Trademark Office